United States Patent [19]

James

[11] Patent Number: 5,776,969
[45] Date of Patent: Jul. 7, 1998

[54] TREATMENT OF SLEEP DISORDERS

[75] Inventor: Steven Parker James, Scotsdale, Ariz.

[73] Assignee: Eli Lilly and Company, Indianapolis, Ind.

[21] Appl. No.: 806,729

[22] Filed: Feb. 27, 1997

[51] Int. Cl.$^6$ ............................................. A61K 31/40
[52] U.S. Cl. .................... 514/418; 514/415; 514/416; 548/302.4
[58] Field of Search ........................... 514/415, 416, 514/417, 418; 548/302.4

[56] References Cited

U.S. PATENT DOCUMENTS

| | | | |
|---|---|---|---|
| 4,584,404 | 4/1986 | Molloy et al. | 564/347 |
| 5,250,571 | 10/1993 | Fuller et al. | 514/651 |
| 5,356,934 | 10/1994 | Robertson et al. | 514/649 |

FOREIGN PATENT DOCUMENTS 687 472  10/1994  European Pat. Off. .

OTHER PUBLICATIONS

Dorsey, et al., *Sleep Research*, 1992, 21, p. 55.
Keck, et al., *Sleep Research*, 1990, 19, p. 66.
Hussaini, et al., *Physiology & Behavior*, vol. 55, No. 2, pp. 391–393, 1994.
B. E.Jones, *Neuroscience*, vol. 40, No. 3, pp. 637–656, 1991.
Oswald, et al., *Br. J. Clin. Pharmac.* (1986), 22, pp. 97–99.
Saletu, et al., *Sleep*, 14(5), pp. 439–447, 1991.
Hendrickse, et al., *Neuropsychopharmacology*, 1994, vol. 10, No. 2, pp. 85–91.
Armitage, et al., *Neuropsychopharmacology*, 1995, vol. 12, No. 2, pp. 159–165.
Schenck, et al., *Sleep*, 15(3), pp. 226–235, 1992.
Dorsey, et al., *Neuropsychopharmacology*, 1996, vol. 14, No. 6, pp. 437–442.
Vercoulen, et al., *The Lancet*, vol. 437, Mar. 30, 1996, pp. 858–861.
Satterlee, et al, *Psychopharmacology Bulletin*, vol. 31, No. 2, 1995, pp. 227–237.
Wallace, et al., *Psychopharmacology*, (1992), 106, pp. 321–329.
Nicholson, et al., *Nueropharmacology*, vol. 27, No. 6, pp. 597–602, 1988.
Pasetl, et al., *Brain Research*, 436 (1987), pp. 92–102.
Fornal, et al., *The Journal of Pharmacology and Experimental Therapeutics*, vol. 225, No. 3, pp. 675–681 (1982).
Slater, et al., Neuropharmacology, vol. 17, pp. 383–389, 1978.
Nicholson, et al., *Neuropsychopharmacology*, 1989, vol. 2, No. 2, pp. 131–143.
Goldstein, et al., *Peptides*, vol. 2, pp. 245–250, 1981.
Artigas, et al., *Archives of General Psychiatry*, vol. 51, No. 3, Mar. 1994, pp. 248–251, XP000605678.

*Primary Examiner*—Johann Richter
*Assistant Examiner*—Ebenezer Sackey
*Attorney, Agent, or Firm*—Robert D. Titus; David E. Boone

[57] ABSTRACT

Disorders of sleep are treated with a combination of a serotonin reuptake inhibitor and a serotonin 1A receptor antagonist.

11 Claims, No Drawings

TREATMENT OF SLEEP DISORDERS

FIELD OF THE INVENTION

The present invention belongs to the fields of pharmacology, medicine and medicinal chemistry, and provides a method of treating disorders of sleep by the administration of a combination of known, safe pharmaceuticals.

BACKGROUND OF THE INVENTION

Over the past twenty years or more, the science of pharmacology has been particularly interested in the physiology of the neurons containing monoamines in the human brain. Discovery has followed discovery in the field and it has now been demonstrated that serotonin, norepinephrine and dopamine interact with a great number of receptors in the brain and control or affect processes which regulate many bodily organs and functions. Serotonin, particularly, has been found to be the key to a large number of processes which reveal themselves in both physiological and psychological functions.

Perhaps the most dramatic discovery in medicinal chemistry in the recent past is fluoxetine, a serotonin reuptake inhibitor, which is extremely effective in the treatment of depression. As a reuptake inhibitor, it increases the availability of serotonin in the synapse by reducing the uptake of serotonin by the serotonin uptake carrier. Dysfunction of the serotonin neurons resulting from excessive uptake results in depression, as well as other pathologies of the central nervous system. Not only is fluoxetine spectacularly effective in depression, it is also effective in treating numerous other conditions.

It has also been discovered that several other drugs are serotonin reuptake inhibitors and have efficacy of the same general type as that of fluoxetine.

While the primary activity of fluoxetine and similar drugs is the inhibition of the reuptake of serotonin, the cascade of monoamine processes in the brain connects serotonin with both norepinephrine and dopamine. Thus, the increase of availability of serotonin results in increased availability of norepinephrine and dopamine as well.

The present inventors have now discovered a previously unsuspected efficacy of the serotonin reuptake inhibitors. Administration of such a drug in combination with an antagonist as the serotonin 1A receptor improves the quality of sleep in patients suffering from a disorder of sleep.

SUMMARY OF THE INVENTION

The invention provides a method of treating disorders of sleep comprising administering to a patient in need of such treatment a first component chosen from the group consisting of fluoxetine, vanlafaxin, citalopram, fluvoxamine, paroxetine, milnacipran and duloxetine in combination with a second component chosen from the group consisting of alprenolol, WAY 100135, WAY 100635, spiperone, pindolol, (S)-UH-301, penbutolol, propranolol, tertatolol, and a compound of the formula

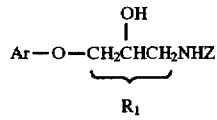

I wherein Ar is

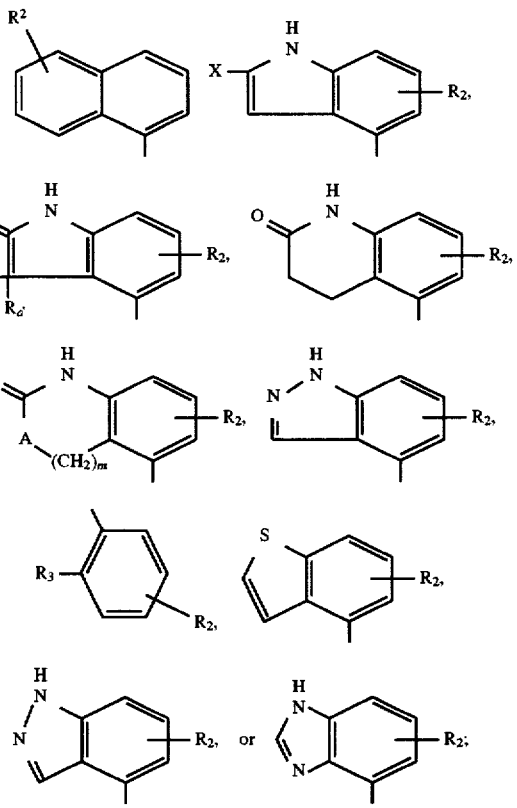

$R_1$ is an optional methyl group substituted on one of the three connecting carbon atoms;

$R_2$ is hydrogen, $C_1$–$C_4$ alkyl, trifluoromethyl, hydroxy, ($C_1$–$C_4$ alkyl)—O—, ($C_1$–$C_4$ alkyl)—S(O)$_p$—, or halo;

$R_3$ is $C_3$–$C_8$ cycloalkyl or a bicycloalkyl group of the formula

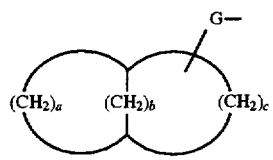

where a and c are independently 1–5, b is 0–5, and (a+c) is greater than 2;

Z is a straight or branched $C_4$–$C_{10}$ alkane, alkene, or alkyne group; ($C_4$–$C_8$ cycloalkyl) optionally substituted with $C_1$–$C_4$ alkyl or phenyl; a bicycloalkyl group of the formula

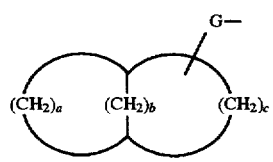

wherein a and c are independently 1–5, b is 0–5, and (a+c) is greater than 2; optionally phenyl substituted $C_2$–$C_{10}$ alkyl where the phenyl group can be optionally substituted with $R_2$ as previously defined; or ($C_1$–$C_4$ alkylidene)—T—(C₁-C₄ alkyl), where T is —O—, —S—, —SO—, or —SO₂—;

where each G is independently a bond or C₁-C₄ alkylidene;

X is —H, —COY, —CN, or C₁-C₄ alkyl;

Y is —OH, —O—(C₁-C₄ alkyl), or —NH₂;

R$_a$ and R$_{a'}$ are independently hydrogen or C₁-C₃ alkyl, or when taken together with the carbon atom to which they are attached form a C₃-C₈ cycloalkyl ring;

p is 0, 1, or 2;

A is —O—, —S—, —NH—, or —NCH₃—; and m is 0, 1, 2, or 3; or a pharmaceutically acceptable salt thereof.

Still further, the invention provides a preferred manner of carrying out the above method of adjunctive therapy wherein the second component is administered in a manner which provides a substantially constant blood level of the second component, which level is sufficient to provide a substantially constant degree of potentiation of the action of the first component. Compositions adapted for carrying out the preferred manner of the invention are also provided.

DESCRIPTION OF PREFERRED EMBODIMENTS

In this document, all temperatures are described in degrees Celsius, and all amounts, ratios of amounts and concentrations are described in weight units unless otherwise stated.

The Compounds

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology* 24, 1211–19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., *Eur. J. Pharmacol.* 41, 153 (1977), and reports of its clinical effectiveness in depression may be found in Dufour et al., *Int. Clin. Psychopharmacol.* 2, 225 (1987), and Timmerman et al., ibid., 239.

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., *Brit. J. Pharmacol.* 60, 505 (1977); and De Wilde et al., *J. Affective Disord.* 4, 249 (1982); and Benfield et al., *Drugs* 32, 313 (1986).

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan et al., *Brit. J. Clin. Pharmacol.* 19, 705 (1985); Laursen et al., *Acta Psychiat. Scand.* 71, 249 (1985); and Battegay et al., *Neuropsychobiology* 13, 31 (1985).

Duloxetine and fluoxetine, as well as the other first components, are known to increase the availability of serotonin (5-HT), dopamine (DA) and norepinephrine (NE), and the second component drugs potentiate that valuable property. The second component drugs have in common the property of being antagonists of the serotonin 1A receptor.

(S)-UH-301 ((S)-5-fluoro-8-hydroxy-2-dipropylaminotetralin) is well known to pharmacologists and pharmaceutical chemists. Hillver et al. taught its synthesis in *J. Med. Chem.* 33, 1541–44 (1990) and Moreau et al., *Brain Res. Bull.* 29, 901–04 (1992) provided considerable in vivo data about the compound.

Alprenolol (1-(1-methylethyl)amino-3-[2-(2-propenyl)phenoxy]-2-propanol) was disclosed by Brandstrom et al., U.S. Pat. No. 3,466,325, which shows its preparation as Example 5.

WAY 100135 (N-(t-butyl)-3-[4-(2-methoxyphenyl)piperazin-1-yl]-2-phenylpropanamide) was disclosed by Abou-Gharbia et al., U.S. Pat. No. 4,988,814, who taught that the compound has affinity for the 5-HT$_{1A}$ receptor. Cliffe et al., *J. Med. Chem.* 36, 1509–10 (1993) showed that the compound is a 5-HT$_{1A}$ antagonist.

WAY 100635 (N-[2-[4-(2-methoxyphenyl)piperazin-1-yl]ethyl]-N-(2-pyridyl)cyclohexanecarboxamide) was put in the literature by Cliffe et al., European Patent Publication 0512755, published Nov. 11, 1992. A number of papers about the compound and its activity as a 5-HT$_{1A}$ antagonist were presented at the IUPHAR Satellite Meeting on Serotonin, Jul. 30, 1994, Chicago, Ill., and abstracts were published.

Spiperone (8-[4-(4-fluorophenyl)-4-oxobutyl]-1-phenyl-1,3,8-triazaspiro[4,5]decan-4-one) is a well-known compound, taught in U.S. Pat. Nos. 3,155,669 and 3,155,670. Its activity as a 5-HT$_{1A}$ antagonist is shown by Middlemiss et al., *Neurosci. and Biobehav. Rev.* 16, 75–82 (1992).

Tertatolol (8-(3-t-butylamino-2-hydroxypropyloxy)triochroman) was disclosed by Malen et al., U.S. Pat. No. 3,960,891, which teaches it to be a blocker of cardiac beta-adrenergic receptors. Its other activities, including the presently used 5-HT$_{1A}$ antagonist activity, have been discovered since the original patents appeared.

Propranolol (1-isopropylamino-3-(1-naphthalenyloxy)-2-propanol) was disclosed by Crowther et al., U.S. Pat. No. 3,337,628 to be a beta-blocker like tertatolol. Again, its other properties are also well known to pharmacologists.

Penbutolol (1-(t-butylamino)-2-hydroxy-3-(2-cyclopentyl-phenoxy)propane) was taught by Ruschig et al., U.S. Pat. No. 3,551,493, which describes it as a beta-blocker. Both the (−) and the (+) enantiomers of penbutolol are of interest; the (−) enantiomer is preferred for the present purpose but both enantiomers and the racemic mixture are included in the word "penbutolol" in this document.

Pindolol (4-(2-hydroxy-3-isopropylaminopropoxy)indole) was disclosed by Troxler et al., U.S. Pat. No. 3,471,515, which describes this compound as well as a beta-blocker. The compound is usually administered as the racemic mixture, but the two enantiomers have been isolated and the (−) enantiomer is preferred if a single isomer product is desired in a given application. Both enantiomers and the racemic mixture are included in the word "pindolol" in this document.

The compounds of formula I are taught by Beedle, et al., U.S. Pat. No. 5,013,761, the description of which is incorporated herein by reference. The synthesis and characteristics, including the 5HT$_{1A}$ antagonist activity, of the compounds is shown in that patent.

The particularly preferred compounds of formula I include, for example, the following individual compounds. It will be understood that the following compounds are typical of those of formula 1 but that the compounds include numerous other valuable species as shown by the previously mentioned U.S. patent. It will be further understood that, while individual salts, and in some cases, enantiomers, are mentioned below and are of particular interest, other salts, and enantiomers, diastereomers, and racemates, are likewise valuable and are included in formula I as agents for the present invention.

1-(4-indolyloxy)-3-cyclohexylamino-2-propanol, maleate salt;

cis-1-(4-indolyloxy)-3-(4-phenylcyclohexyl-amino)-2-propanol, oxalate salt;

1-(4-indolyloxy)-3-(2-phenylethylamino)-2-propanol, oxalate salt;

1-(4-indolyloxy)-3-(3-phenylpropylamino)-2-propanol, oxalate salt;

1-(4-indolyloxy)-3-(4-phenylbutylamino)-2-propanol, oxalate salt;

1-(4-indolyloxy)-3-cyclopentylamino-2-propanol, maleate salt;

1-(4-indolyloxy)-3-cycloheptylamino-2-propanol;

(S)-(−)-1-(4-indolyloxy)-3-cyclohexylamino-2-propanol, maleate salt;

(+)-1-(4-indolyloxy)-3-cyclohexylamino-2-propanol, maleate salt;

1-(4-indolyloxy)-3-(3-methylcyclohexylamino)-2-propanol;

1-(4-indolyloxy)-3-(4-methylcyclohexylamino)-2-propanol;

1-(4-indolyloxy)-3-(5-phenylpentylamino)-2-propanol, oxalate salt;

1-(4-indolyloxy)-3-(6-phenylhexylamino)-2-propanol, oxalate salt;

1-(4-indolyloxy)-3-(2,3-dimethylcyclohexyl-amino)-2-propanol, oxalate salt;

(+−)-1-(4-indolyloxy)-3-(3-pentylamino)-2-propanol;

(R)-(+)-1-(4-indolyloxy)-3-cyclohexylamino-2-propanol, butanedioate salt;

(R)-(−)-1-(4-indolyloxy)-3-cyclohexylamino-2-propanol, butanedioate salt;

1-(2-trifluoromethyl-4-benzimidazolyl)-3-(4-phenylbutylamino)-2-propanol;

(exo)-1-(4-indolyloxy)-3-(norbornylamino)-2-propanol;

(endo)-1-(4-indolyloxy)-3-(norbornylamino)-2-propanol;

1-(1-napthalenyloxy)-3-cycloheptylamino-2-propanol, oxalate salt;

1-(2-cyclopentylphenoxy)-3-cycloheptylamino-2-propanol, oxalate salt;

1-(2-cyclohexylphenoxy)-3-cyclooctylamino-2-propanol, oxalate salt;

1-(2-cycloheptylphenoxy)-3-(1,2,3-trimethyl-2-propylamino)-2-propanol, oxalate salt; and 1-(2-cyclopropylphenoxy)-3-(1,1-dimethylbutylamino)-2-propanol, oxalate salt.

The group of the compounds of formula I wherein the group Ar is indolyl or substituted indolyl constitutes a further preferred class of 5-HT$_{1A}$ antagonists; and the compounds of formula 1 wherein Z is (C$_4$–C$_8$ cycloalkyl) optionally substituted with C$_1$–C$_4$ alkyl or phenyl; or Z represents optionally phenyl substituted C$_2$–C$_{10}$ alkyl where the phenyl group can be optionally substituted with R$_2$; constitute further particularly preferred classes of compounds for use in the present invention.

All of the U.S. patents which have been mentioned above in connection with compounds used in the present invention are incorporated herein by reference.

While all combinations of first component and second component compounds are useful and valuable, certain combinations are particularly valued and are preferred, as follows:

fluoxetine/pindolol duloxetine/pindolol fluoxetine/penbutolol duloxetine/penbutolol fluoxetine/propranolol duloxetine/propranolol fluoxetine/tertatolol duloxetine/tertatolol fluoxetine/4-(2-hydroxy-3-cyclohexylaminopropoxy) indole duloxetine/4-(2-hydroxy-3-cyclohexylaminopropoxy) indole In general, combinations and methods of treatment using fluoxetine or duloxetine as the first component are preferred.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Administration

The dosages of the drugs used in the present invention must, in the final analysis, be set by the physician in charge of the case, using knowledge of the drugs, the properties of the drugs in combination is determined in clinical trials, and the characteristics of the patient, including diseases other than that for which the physician is treating the patient. General outlines of the dosages, and some preferred dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Pindolol: from about 1 to about 60 mg once-thrice/day; preferred, from about 5 to about 60 mg once-thrice/day; also preferred, from about 1 to about 10 mg twice/day; or from about 4 to about 20 mg/day as a sustained release dosage form;

Penbutolol: from about 2 to about 80 mg once/day; preferred, from about 10 to about 80 mg once/day; also preferred, from about 2 to about 20 mg once/day;

Propranolol: from about 10 to about 240 mg once-twice/day; preferred, from about 10 to about 120 mg twice/day; also preferred, from about 40 to about 240 mg once-twice/day;

4-(2-Hydroxy-3-cyclohexylaminopropoxy)indole: from about 1 to about 50 mg once-twice/day; preferred, from about 1 to about 10 mg twice/day.

In more general terms, one would create a combination of the present invention by choosing a dosage of first component compound according to the spirit of the above guideline, and choosing a dosage of the second component compound in the general range of from about 1 to about 250 mg/dose. More preferred dosages, depending on the compound, would be from about 1 to about 100 mg/dose, and even more preferred dosages would be likely to be found in the range of from about 1 to about 50 mg/dose, ideally from about 1 to about 25 mg/dose.

The adjunctive therapy of the present invention is carried out by administering a first component together with one of the second component compounds in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a first component and a second component compound are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

The second component compounds, taken as a class, have short lives in the body and, accordingly, provide only short periods of activity following each dose. For example, pindolol is routinely administered twice/day in the prior art, and it has been administered even more often. In the context of the present invention, it is therefore preferred to administer the second component compounds in a manner which supplies a substantially constant blood level of the second component in the body of the patient, at a sufficiently high level to provide a substantially constant degree of potentiation of the action of the first component.

It is not intended, of course, that the present invention or any method of human treatment can provide a truly constant blood level and degree of potentiation. Biological processes always vary and prevent precisely constant results. The term "substantially constant" is used herein to refer to administration resulting in blood levels and degrees of potentiation which are sufficiently constant as to provide continuous improved efficacy over a treatment day, compared to the efficacy of the first component compound alone. Another way to consider substantially constant potentiation is by comparing the availability of serotonin, norepinephrine and dopamine in the brain of the patient. By "substantially constant" in such terms is meant a condition where the peak and the valley of availability differ by no more than about a factor of 2 over the course of a treatment day. Another way to consider "substantially constant" is a condition where the peak and valley differ by no more than about a factor of 1.5; or they differ by no more than a range of from about 1.5 to about 3.

Such administration of the second component may be provided by means known to pharmaceutical scientists. For example, the total daily dosage of a second component may be formulated in a manner which provides a substantially constant flow of compound to the patient. To consider only pindolol, at least the following references teach sustained release formulations: German Patent 3632201, capsules; Swiss Patent 634990, tablets; German Patent 3237945, buccal tape; German Patent 2732335, tablets; U.S. Pat. No. 5,260,066, cryogels; European Patent Publication 361894, liposomes; Japanese Patent 84-66710, transdermal patches. Pharmaceutical scientists are acquainted in modern practice with the manners of adjusting a sustained release formulation to provide the desired rate of administration of a given compound and such formulations can be prepared by the skill of the pharmaceutical art of the compounds used as second components here.

Such formulations of a second component compound may be combined in a single dosage form with the chosen first component compound. For example, a small tablet or pellets of the second component, formulated to provide constant availability of the compound, may be combined, for example in a capsule, with the first component compound. Alternatively, a transdermal patch may be prepared which has a relatively rapidly releasing area of first component, and a relatively slowly releasing area of second component. Still further, a suspension may be prepared in which the first component is present as particles of pure compound, and the particles of the second component are coated to provide sustained release in the body. In such manners, the availability of the second component may be adjusted to provide the desired substantially constant blood levels and, hence, substantially constant potentiation of the first component. Compositions so adapted for providing substantially constant potentiation of the first component are preferred compositions of the present invention.

The inert ingredients and manner of formulation of the adjunctive pharmaceutical compositions are conventional, except for the presence of the combination of the first component and the second component compound. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspension. In general, compositions contain from about 0.5% to about 50% of the compounds in total, depending on the desired doses and the type of compositions to be used. The amount of the compounds, however, is best defined as the effective amount, that is, the amount of each compound which provides the desired dose to the patient in need of such treatment. The activity of the adjunctive combinations do not depend on the nature of the composition, so the compositions are chosen and formulated solely for convenience and economy. Any of the combinations may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch or many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. It is preferred to formulate duloxetine and duloxetine-containing combinations as enteric compositions, and even more preferred to formulate them as enteric pellets.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

EXAMPLE 10 mg Duloxetine base/capsule

| Bill of Materials | |
|---|---|
| Beads | |
| Sucrose - starch nonpareils, 20–25 mesh | 60.28 mg |
| Duloxetine layer | |
| Duloxetine | 11.21 |
| Hydroxypropylmethylcellulose | 3.74 |
| Separating layer | |
| Hydroxypropylmethylcellulose | 2.51 |
| Sucrose | 5.00 |
| Talc, 500 mesh | 10.03 |
| Enteric layer | |
| HPMCAS, LF grade, Shin-Etsu Chemical Co., Tokyo, Japan | 25.05 |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60 mg |

The duloxetine layer was build up by suspending duloxetine in a 4% w/w solution of the hydroxypropylmethylcellulose in water, and milling the suspension with a CoBall Mill (Fryma Mashinen AG, Rheinfelden, Switzerland) model MS-12. A fluid bed dryer with a Wurster column was used to make this product, at a batch size of 1.0 kg. The separating layer was added from a 4% w/w solution of the hydroxypropylmethylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HMPCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially complete pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/hydroxypropylmethylcellulose solution containing titanium dioxide and propylene glycol as plasticizer. The pellets were completely dried in the fluid bed dryer and then were then filled in size 3 gelatin capsules.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or particularly dissolve, which is held in contact with the skin by a film which protects the composition. Many patients have appeared in the field recently. Other, more complicated patch compositions are also in use, particularly those having a membrane pierced with innumerable pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
|---|---|
| Fluoxetine, racemic, hydrochloride | 20 mg |
| Pindolol | 30 |
| Starch, dried | 200 |
| Magnesium stearate | 10 |
| Total | 260 mg |

Formulation 2

A tablet is prepared using the ingredients below:

|  | Quantity (mg/capsule) |
|---|---|
| Fluoxetine, racemic, hydrochloride | 10 |
| (−)-Penbutolol | 40 |
| Cellulose, microcrystalline | 400 |
| Silicon dioxide, fumed | 10 |
| Stearic acid | 5 |
| Total | 465 mg |

The components are blended and compressed to form tablets each weighing 465 mg.

Formulation 3

An aerosol solution is prepared containing the following components:

|  | Weight |
|---|---|
| (+)-Duloxetine, hydrochloride | 10 |
| Pindolol | 10 |
| Ethanol | 25.75 |
| Propellant 22 | 70.00 |
| (Chlorodifluoromethane) |  |
| Total | 115.75 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 80 mg of active ingredient, are made as follows:

|  |  |
|---|---|
| (+)-Duloxetine, hydrochloride | 20 mg |
| (−)-Penbutolol | 60 mg |
| Starch | 45 mg |
| Microcrystalline cellulose | 35 mg |
| Polyvinylpyrrolidone | 4 mg |
| (as 10% solution in water) |  |
| Sodium carboxymethyl starch | 4.5 mg |
| Magnesium stearate | 0.5 mg |
| Talc | 1 mg |
| Total | 170 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 170 mg.

Formulation 5

Capsules, each containing 130 mg of active ingredient, are made as follows:

|  |  |
|---|---|
| Fluoxetine, racemic, hydrochloride | 30 mg |
| Propranolol | 100 mg |
| Starch | 59 mg |
| Microcrystalline cellulose | 59 mg |
| Magnesium stearate | 2 mg |
| Total | 250 mg |

The active ingredient, cellulose, starch, and magnesium stearate are blended, passed through a No. 45 mesh U.S. sieve, and filled into hard gelatin capsules in 250 mg quantities.

Formulation 6

Suppositories, each containing 45 mg of active ingredient, are made as follows:

| | |
|---|---|
| (+)-Duloxetine, hydrochloride | 5 mg |
| Propranolol | 40 mg |
| Saturated fatty acid glycerides | 2,000 mg |
| Total | 2,045 mg |

The active ingredient in passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 70 mg of active ingredient per 5 ml dose, are made as follows:

| | |
|---|---|
| Fluoxetine, racemic, hydrochloride | 10 mg |
| Propranolol | 60 mg |
| Sodium carboxymethyl cellulose | 50 mg |
| Syrup | 1.25 mg |
| Benzoic acid solution | 1.10 mg |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| (+)-Duloxetine, hydrochloride | 10 mg |
| Propranolol | 20 mg |
| Isotonic saline | 1,000 ml |

Benefit of the Invention

The benefit of the present invention is its ability to alleviate or even cure disorders of sleep, which will be discussed below in some detail. The disorders which are to be treated according to the present invention are of a psychiatric nature, and are to be diagnosed, and the treatment prescribed, by psychiatrists and other physicians. It will be understood that the patient and doctor cannot expect that such treatment will effect a cure in all cases. However, treatment according to the present invention, perhaps combined with other treatments such as psychiatric consultation and analysis, lifestyle modification, and perhaps other treatments for concomitant disorders, will be found to alleviate the disorder to sleep, producing a substantial benefit to the patient. In some cases, the benefit will be in the form of an alleviation of the unpleasant symptoms of the disorders, and in other cases substantial or even complete diminution of the symptoms will be obtained, amounting to complete cure of the disorder.

Specific disorders of sleep to be treated according to the present invention will be described according to the nomenclature in the *Diagnostic and Statistical Manual of Mental Disorders*, 4th Edition (1994),published by the American Psychiatric Association. Sleep disorders which are of particular interest with relation to the present invention are primary insomnia (DSM-IV Code 307.42), primary hypersomnia (307.44), narcolepsy (347), circadian rhythm sleep disorder (307.45), parasomnias including nightmare disorder (307.47), sleep terror disorder (307.46), and sleepwalking disorder (307.46), sleep disorders related to another mental disorder (307.42 and 307.44), sleep disorders due to a general medical condition (780.xx) and substance-induced sleep disorders.

Further description and discussion of sleep disorders are found in the *International Classification of Sleep Disorders: Diagnostic and Coding Manual* (1990), published by the American Sleep Disorders Association.

No doubt the best known disorder of sleep is primary insomnia, the difficulty in initiating or maintaining sleep, sometimes also manifested by the patient's being asleep but not being rested or restored. Most often patients report a combination of difficulty falling asleep and intermittent wakefulness during sleep. A preoccupation with and distress die to the inability to sleep may create a cycle: the more the patient strives to sleep, the more frustrated the individual becomes and the less he or she is able to sleep. Chronic insomnia may lead to decreased feelings of well-being during the day, with decreased attention, energy and concentration and an increase in fatigue. Personal, social and occupational problems may develop and patients may have accidents. The sleep disturbance constitutes a risk factor for subsequent mood disorders and anxiety disorders, as well as a risk factor for inappropriate use of hypnotics, alcohol, anxiolytics and caffeine and other stimulants. The true prevalence of primary insomnia among the general population is unknown, but may be quite high. About 15 . 25% of patients presented to sleep clinics complaining of insomnia are found to have primary insomnia.

The DSM-IV lists the diagnostic criteria for primary insomnia as follows:

A. The predominant complaint is difficulty initiating or maintaining sleep, or nonrestorative sleep, for at least 1 month.

B. The sleep disturbance (or associated daytime fatigue) causes clinically significant distress or impairment in social, occupational, or other important areas of functioning.

C. The sleep disturbance does not occur exclusively during the course of Narcolepsy, Breathing-Related Sleep Disorder, Circadian Rhythm Sleep Disorder, or a Parasomnia.

D. The disturbance does not occur exclusively during the course of another mental disorder (e.g., Major Depressive Disorder, Generalized Anxiety Disorder, a delirium).

E. The disturbance is not due to the direct physiological effects of a substance (e.g., a drug of abuse, a medication) or a general medical condition.

Primary hypersomnia is evidenced by excessive sleepiness in the form of either prolonged sleep episodes or by frequent daytime sleep episodes. The excessive sleepiness is sufficiently severe to cause distress or impairment in social, occupational and other important aspects of the patient's life. Such patients sleep from 8–12 hours every night, and often have difficulty awakening. Daytime naps tend to be relatively long as well, and are not refreshing. Hypersomnia patients' daytime sleep episodes can be embarrassing and even dangerous, if the individual is operating a machine, for example, and the patient's low alertness leads to poor efficiency and other difficulties during daytime activities.

Of course, the normal range of sleep duration varies considerably. Individuals who naturally require a relatively large amount of sleep, but do not have excessive daytime sleepiness, are not suffering from hypersomnia, and the diagnosis is readily made. The diagnostic criteria for hypersomnia are as follows:

A. The predominant complaint is excessive sleepiness for at least 1 month (or less if recurrent) as evidenced by either prolonged sleep episodes or daytime sleep episodes that occur almost daily.

B. The excessive sleepiness causes clinically significant distress or impairment in social, occupational, or other important areas of functioning.

C. The excessive sleepiness is not better accounted for by insomnia and does not occur exclusively during the course of another Sleep Disorder (e.g. Narcolepsy, Breathing-Related Sleep Disorder, Circadian Rhythm Sleep Disorder, or a Parasomnia) and cannot be accounted for by an inadequate amount of sleep.

D. The disturbance does not occur exclusively during the course of another mental disorder.

E. The disturbance is not due to the direct physiological effects of a substance (e.g., a drug of abuse, a medication) or a general medical condition.

Narcolepsy is characterized by repeated attacks of refreshing sleep, usually accompanied with cataplexy. Episodes of sleepiness are often irresistible, resulting in falling asleep while driving or carrying on a conversation. Sleep episodes are usually brief but can last up to an hour, and frequently recur 2–6 times per day.

Patients with narcolepsy may avoid social activities and their functioning of all kinds can be severely limited and impaired. Patients are at considerable risk of injury because of falling asleep in dangerous situations.

The degree of daytime sleepiness may be similar in patients with narcolepsy and primary hypersomnia, but narcolepsy patients have more urgent sleep attacks and cataplexy, sleep-related hallucinations and sleep paralysis are confined to narcolepsy patients. The diagnostic criteria for narcolepsy are as follows:

A. Irresistible attacks of refreshing sleep that occur daily over at least 3 months.

B. The presence of one or both of the following:
  (1) cataplexy (i.e., brief episodes of sudden bilateral loss of muscle tone, most often in association with intense emotion)
  (2) recurrent intrusions of elements of rapid eye movement (REM) sleep into the transition between sleep and wakefulness, as manifested by either hypnopompic or hypnagogic hallucinations or sleep paralysis at the beginning or end of sleep episodes.

C. The disturbance is not due to the direct physiological effects of a substance (e.g., a drug of abuse, a medication) or other general medical condition.

Circadian rhythm sleep disorder does not result directly from the mechanisms generating sleep and wakefulness, but is a pattern of sleep disruption resulting from incongruity between the patient's needs to maintain a schedule, and his or her internal sleep-waking system. Individuals with the disorder may be excessively sleepy at some times of the day, and complain of insomnia at other times.

Circadian rhythm sleep disorder may be of the jet lag type, which is self-explanatory, the shift work type, or the delayed sleep phase type, wherein the patient's sleep-wake cycle is delayed relative to the needed schedule. Such individuals are chronically sleep-deprived but their sleep is normal once it is initiated. The familiar people who are "morning type" and "night owls" have a circadian rhythm disorder which in effect deprives them of part of a normal waking day. The diagnostic criteria for circadian rhythm sleep disorder are as follows:

A. A persistent or recurrent pattern of sleep disruption leading to excessive sleepiness or insomnia that is due to a mismatch between the sleep-wake schedule required by a person's environment and his or her circadian sleep-wake pattern.

B. The sleep disturbance causes clinically significant distress or impairment in social, occupational, or other important areas of functioning.

C. The disturbance does not occur exclusively during the course of another Sleep Disorder or other mental disorder.

D. The disturbance is not due to the direct physiological effects of a substance (e.g., a drug of abuse, a medication) or a general medical condition.

Parasomnias are disorders which are brought about by activation if inappropriate sections of the nervous system during sleep or sleep-waking transitions. Parasomnias include nightmare disorder, sleep terror disorder and sleepwalking disorder, the unpleasant nature of which are described by their mere names. The diagnostic criteria for these disorders further describe the disruption which they cause:

Nightmare Disorder

A. Repeated awakenings from the major sleep period or naps with detailed recall of extended and extremely frightening dreams, usually involving threats to survival, security, or self-esteem. The awakenings generally occur during the second half of the sleep period.

B. On awakening from the frightening dreams, the person rapidly becomes oriented and alert (in contrast to the confusion and disorientation seen in Sleep Terror Disorder and some forms of epilepsy).

C. The dream experience, or the sleep disturbance resulting from the awakening, causes clinically significant distress or impairment in social, occupational, or other important areas of functioning.

D. The nightmares so not occur exclusively during the course of another mental disorder (e.g., a delirium, Posttraumatic Stress Disorder) and are not due to the direct physiological effects of a substance (e.g., a drug or abuse, a medication) or a general medical condition.

Sleep Terror Disorder

A. Recurrent episodes of abrupt awakening from sleep, usually occurring during the first third of the major sleep episode and beginning with a panicky scream.

B. Intense fear and signs of autonomic arousal, such as tachycardia, rapid breathing, and sweating, during each episode.

C. Relative unresponsiveness to efforts of others to comfort the person during the episode.

D. No detailed dream is recalled and there is amnesia for the episode.

E. The episodes cause clinically significant distress or impairment in social, occupational, or other important areas of functioning.

F. The disturbance is not due to the direct physiological effects of a substance (e.g., a drug of abuse, a medication) or a general medical condition.

Sleepwalking Disorder

A. Repeated episodes of rising from bed during sleep and walking about, usually occurring during the first third of the major sleep episode.

B. While sleepwalking, the person has a blank staring face, is relatively unresponsive to the efforts of others to communicate with him or her, and can be awakened only with great difficulty.

C. On awakening (either from the sleepwalking episode or the next morning), the person has amnesia for the episode.

D. Within several minutes after awakening from the sleepwalking episode, there is not impairment of mental activity or behavior (although there may initially be a short period of confusion or disorientation).

E. The sleepwalking causes clinically significant distress or impairment in social, occupational, or other important areas of functioning.

F. The disturbance is not due to the direct physiological effects of a substance (e.g., a drug of abuse, a medication) or a general medical condition.

Disorders of sleep frequently occur in relation to or because of another mental disorder, or a general medical condition. Both insomnia and hypersomnia frequently are related to such other conditions. The symptoms with which the patient presents in such disorders are substantially the same as the symptoms of primary insomnia or primary hypersomnia, but the patient's history and other diagnoses bring out the relation to the other mental or general medical conditions.

The following diagnostic criteria illustrate the circumstances of patients with insomnia or hypersomnia related to another mental disorder:

Insomnia Related to . . . [Axis I or Axis II Disorder]

A. The predominant complaint is difficulty initiating or maintaining sleep, or nonrestorative sleep, for at least 1 month that is associated with daytime fatigue or impaired daytime functioning.

B. The sleep disturbance (or daytime sequelae) causes clinically significant distress or impairment in social, occupational, or other important areas of functioning.

C. The insomnia is judged to be related to another Axis I or Axis II disorder (e.g., Major Depressive Disorder, Generalized Anxiety Disorder, Adjustment Disorder With Anxiety), but is sufficiently server to warrant independent clinical attention.

D. The disturbance is not better accounted for by another Sleep Disorder (e.g., Narcolepsy, Breathing-Related Sleep Disorder, a Parasomnia).

E. The disturbance is not due to the direct physiological effects of a substance (e.g., a drug of abuse, a medication) or a general medical condition.

Hypersomnia Related to . . . [Axis I or Axis II Disorder]

A. The predominant complaint is excessive sleepiness for at least 1 month as evidenced by either prolonged sleep episodes or daytime sleep episodes that occur almost daily.

B. The excessive sleepiness causes clinically significant distress or impairment in social, occupational, or other important areas of functioning.

C. The hypersomnia is judged to be related to another Axis I or Axis II disorder (e.g., Major Depressive Disorder, Dysthymic Disorder), but is sufficiently severe to warrant independent clinical attention.

D. The disturbance is not better accounted for by another Sleep Disorder (e.g., Narcolepsy, Breathing-Related Sleep Disorder, a Parasomnia) or by an inadequate amount of sleep.

E. The disturbance is not due to the direct physiological effects of a substance (e.g., a drug of abuse, a medication) or a general medical condition.

The following diagnostic criteria illustrate insomnia or hypersomnia related to or due to a general medical condition.

A. A prominent disturbance in sleep that is sufficiently severe to warrant independent clinical attention.

B. There is evidence from the history, physical examination, or laboratory findings that the sleep disturbance is the direct physiological consequence of a general medical condition.

C. The disturbance is not better accounted for by another mental disorder (e.g., an Adjustment Disorder in which the stressor is a serious medical illness).

D. The disturbance does not occur exclusively during the course of a delirium.

E. The disturbance does not meet the criteria for Breathing-Related Sleep Disorder or Narcolepsy.

F. The sleep disturbance causes clinically significant distress or impairment in social, occupational, or other important areas of functioning.

Disorders of sleep, finally, may be induced by inappropriate use of substances, such as alcohol, drugs of abuse, or pharmaceuticals. Amphetamines, caffeine, cocaine, opioids, sedatives, hypnotics and anxiolytics may be associated with substance-induced sleep disorders. Such sleep disorders can occur during intoxication, during withdrawal from the substance, or both. Both insomnia and hypersomnia are found in patients with substance-induced sleep disorders. The treatment of substance-induced sleep disorders (as well as that of sleep disorders due to a general medical condition) may be complicated by treatment of the substance addiction or the medical condition with drugs which cause or exacerbate a sleep complaint in themselves.

The following diagnostic criteria more precisely describes substance-induced sleep disorder.

A. A prominent disturbance in sleep that is sufficiently severe to warrant independent clinical attention.

B. There is evidence from the history, physical examination, or laboratory findings of either (1) or (2):
  (1) the symptoms in Criterion A developed during, or within a month of, Substance Intoxication or Withdrawal
  (2) medication use is etiologically related to the sleep disturbance C. The disturbance is not better accounted for by a Sleep Disorder that is not substance induced. Evidence that the symptoms are better accounted for by a Sleep Disorder that is not substance induced might include the following: the symptoms precede the onset of the substance use (or medication use); the symptoms persist for a substantial period of time (e.g., about a month) after the cessation of acute withdrawal or severe intoxication, or are substantially in excess of what would be expected given the type or amount of the substance used or the duration of use; or there is other evidence that suggests the existence of an independent non-substance-induced Sleep disorder (e.g., a history of recurrent non-substance-related episodes).

D. The disturbance does not occur exclusively during the course of a delirium.

E. The sleep disturbance causes clinically significant distress or impairment in social, occupational, or other important areas of functioning.

Since the present method of treatment of sleep disorders is quite safe and free of hazardous side effects, treatment according to this invention may be begun as soon as a patient is diagnosed, and may be continued for relatively long periods of time. Often, of course, patients will respond to psychiatric drugs comparatively quickly, and it will be possible to discontinue such treatment without the patient's relapsing into the disorder. Frequently that happy outcome is obtained with the present treatment. However, should it be necessary to continue the present treatment for an extended period of time, such as several months or a year or more, there is no reason to refrain from such continued treatment.

Experimental Results

Representative combinations of the present invention have been tested in conscious experimental animals and the surprising results of the testing demonstrate the mechanism which results in the benefit of the invention. The tests were carried out as follows.

Microdialysis Assays of Monoamines

Sprague-Dawley rats (Harlan or Charles River) weighing 270–300 grams were surgically implanted with microdialysis probes under chloral hydrate/pentobarbital anesthesia (170 and 36 mg/kg i.p. in 30% propylene glycol, 14% ethanol) (Perry and Fuller, Effect of fluoxetine on serotonin and dopamine concentration in rat hypothalamus after administration of fluoxetine plus L-5-hydroxytryptophan, Life Sci., 50, 1683–90 (1992)). A David Kopf stereotaxic instrument was used to implant the probe unilaterally in the hypothalamus at coordinates rostral −1.5 mm, lateral −1.3 mm, and ventral −9.0 mm (Paxinos and Watson, 1986). After a 48 hour recovery period, rats were placed in a large plastic bowl with a mounted liquid swivel system (CMA/120 system for freely moving animals, Bioanalytical systems, West Lafayette, Ind.). Filtered artificial cerebrospinal fluid (CSF) (150 mM NaCl, 3.0 mM KCl, 1.7 mM CaCl2, and 0.9 mM MgCl2) was perfused through the probe at a rate of 1.0 μl/min. The output dialysate line was fitted to a tenport HPLC valve with a 20 μl loop. At the end of each 30 minute sampling period, dialysate collected in the loop was injected on an analytical column (Spherisorb 3μ ODS2, 2×150 mm, Keystone Scientific).

The method used to measure monoamines was as described by Perry and Fuller (1993). Briefly, dialysate collected in the 20 μl loop was assayed for 5-HT, NE and DA. The 20 μl injection went onto the column with a mobile phase which resolved NE, DA, and 5-HT: 75 mM potassium acetate, 0.5 mM ethylenediaminetetraacetic acid, 1.4 mM sodium octanesulfonic acid and 8% methanol, pH 4.9. The mobile phase for the amine column was delivered with a flow programmable pump at an initial flow rate of 0.2 ml/min increasing to 0.3 ml/min at 5 min then decreasing back to 0.2 ml/min at 26 min with a total run time of 30 min. Flow programming was used to elute the 5-HT within a 25 min time period. The electrochemical detector (EG&G, Model 400) for the amine column was set at a potential of 400 mV and a sensitivity of 0.2 nA/V. The data was collected and analyzed with a Hewlett-Packard HP1000 chromatography system which measured peak heights and calculated sample concentrations. Basal levels were measured for at least 90 minutes prior to drug administration. The drugs were prepared in filtered deionized water and administered (volume 0.25–0.3 ml) at the doses stated in the results below.

Evaluation and Statistical Analyses

Extracellular levels of the amines in microdialysates were calculated by comparing peak heights with those of 50 pmole standards. The mean value of the four samples immediately preceding drug administration served as the basal level for each experiment and data was converted to percent of basal. Paired t-tests were used to compare the mean of the basal values from the time point immediately preceding drug administration to those of each time point thereafter.

The data has been rounded to make the trends more visible.

Test 1

In this test, the combination therapy comprised fluoxetine as the hydrochloride of the racemate and 4-(2-hydroxy-3-cyclohexylaminopropoxy)indole, maleate. The rats were prepared as described above, and the indole was administered subcutaneously at 3 mg/kg 100 minutes after the start of the experiment. Fluoxetine was administered intraperitoneally at 10 mg/kg, together with a second dose of the indole at 3 mg/kg, 210 minutes after the start of the experiment. Each data point reported here represents a single animal.

The 5-HT level measured in the dialysate declined upon administration of the indole, as low as about 50% of baseline, and was at about 80% of baseline at 210 minutes. It increases sharply upon administration of fluoxetine and was measured at about 410% of baseline at 240 minutes, about 450% of baseline at 270 and about 460% at 300 minutes, and at about 390% of baseline at 330 minutes.

The NE level increased upon administration of the indole, as high at about 180% of baseline, and declined nearly to baseline by 210 minutes. Upon administration of fluoxetine, it increased to about 500% of baseline at 240 minutes, and declined to about 340%, 280% and 200% of baseline at 270, 300 and 330 minutes respectively.

Similarly, DA level increased to about 210% of baseline at 120 minutes and declined to near baseline at 210 minutes. Administration of fluoxetine increased the DA level to about 1430% of baseline at 240 minutes, about 840% of baseline at 270 minutes, about 530% at 300 minutes, and about 330% at 330 minutes.

Test 2

In this test, the drugs were (+)-duloxetine, hydrochloride, administered at 4 mg/kg, and (−)-pindolol, at 5 mg/kg. The test was carried out in the same manner as Test 1, administering the (−)-pindolol first at 120 minutes after start of experiment, and then the duloxetine together with a second dose of (−)-pindolol at 5 mg/kg at 210 minutes. The results are shown below as percent of baseline of the three monoamines, at various times after the start of the experiment. Each data point represents the average of three or more animals.

| Time | 5-HT | NE | DA |
|---|---|---|---|
| 120 min. | 80% | 90% | 90% |
| 150 | 90 | 100 | 90 |
| 180 | 110 | 120 | 70 |
| 210 | 100 | 110 | 100 |
| 240 | 240 | 350 | 230 |
| 270 | 340 | 230 | 170 |
| 300 | 360 | 210 | 140 |
| 330 | — | 230 | 150 |
| 360 | 330 | 170 | 150 |

Test 3

This test was carried out as described in Test 1, using 4-(2-hydroxy-3-cyclohexylaminopropoxy)indole, maleate, at 3 mg/kd administered at 120 minutes, and (+)-duloxetine, hydrochloride, at 4 mg/kg administered with a second dose of the indole at 3 mg/kg, at 270 minutes. Results are reported

| Time | 5-HT | NE | DA |
|---|---|---|---|
| 120 min. | 90% | 100% | 70% |
| 150 | 130 | 160 | 150 |
| 180 | 130 | 140 | 130 |
| 210 | 80 | 140 | 110 |
| 240 | 90 | 130 | 100 |
| 270 | 80 | 150 | 110 |
| 300 | 650 | 580 | 410 |
| 330 | 670 | 390 | 280 |
| 360 | 590 | 450 | 240 |
| 390 | 490 | 320 | 210 |
| 420 | 440 | 290 | 200 |

We claim:

1. A method of treating disorders of sleep comprising administering to a patient in need of such treatment a first component chosen from the group consisting of fluoxetine, venlafaxine, citalopram, fluvoxamine, paroxetine, milnacipran and duloxetine in combination with a second component chosen from the group consisting of alprenolol, WAY 100135, WAY 100635, spiperone, pindolol, (S)-UH-301, penbutolol, propranolol, tertatolol, and a compound of the formula $$Ar-O-CH_2CHCH_2NHZ$$
$$\quad\quad\quad\quad\quad\;\; |$$
$$\quad\quad\quad\quad\quad\; OH$$
$$\quad\quad\quad\quad\quad\quad\quad\quad R_1$$

I wherein Ar is

[structure]

$R_1$ is an optional methyl group substituted on one of the three connecting carbon atoms;

$R_2$ is hydrogen, $C_1$–$C_4$ alkyl, trifluoromethyl, hydroxy, ($C_1$–$C_4$ alkyl)—O—, ($C_1$–$C_4$ alkyl)—S(O)$_p$—, or halo;

Z is a straight or branched $C_4$–$C_{10}$ alkane, alkene, or alkyne group; ($C_4$–$C_8$ cycloalkyl) optionally substituted with $C_1$–$C_4$ alkyl or phenyl; a bicycloalkyl group of the formula

[structure]

wherein a and c are independently 1–5, b is 0–5, and (a+c) is greater than 2; optionally phenyl substituted $C_2$–$C_{10}$ alkyl where the phenyl group can be optionally substituted with $R_2$ as previously defined; or ($C_1$–$C_4$ alkylidene)-T-($C_1$–$C_4$ alkyl), where T is —O—, —S—, —SO—, or —SO$_2$—;

where

G is independently a bond or $C_1$–$C_4$ alkylidene;

X is —H, —COY, —CN, or $C_1$–$C_4$ alkyl,

Y is —OH, O ($C_1$–$C_4$ alkyl), or —NH$_2$;

$R_a$ and $R_{a'}$ are independently hydrogen or $C_1$–$C_3$ alkyl, or when taken together with the carbon atom to which they are attached form a $C_3$–$C_8$ cycloalkyl ring; and p is 0, 1, or 2;

or a pharmaceutically acceptable salt thereof.

2. A method of claim 1 wherein the first component is fluoxetine or duloxetine.

3. A method of claim 2 wherein the first component is duloxetine.

4. A method of claim 2 wherein the first component is fluoxetine.

5. A method of any one of claims 1–4 wherein the second component is chosen from the group consisting of pindolol, penbutolol, propranolol, tertatolol, and 4-(2-hydroxy-3-cyclohexylaminopropoxy)indole.

6. A method of claim 5 wherein the second component is pindolol.

7. A method of claim 1 wherein the second component is administered in a manner which provides a substantially constant blood level of the second component, which level is sufficient to provide a substantially constant degree of potentiation of the action of the first component.

8. A method of claim 7 wherein the first component is fluoxetine or duloxetine.

9. A method of claim 7 wherein the first component is fluoxetine.

10. A method of claim 7 wherein the first component is duloxetine.

11. A method of any one of claims 7–10 wherein the second component is pindolol.

* * * * *